United States Patent
Minowa

(10) Patent No.: US 10,502,696 B2
(45) Date of Patent: Dec. 10, 2019

(54) WATER VAPOR OBSERVING APPARATUS

(71) Applicant: Furuno Electric Co., Ltd., Nishinomiya (JP)

(72) Inventor: Masahiro Minowa, Nishinomiya (JP)

(73) Assignee: Furuno Electric Co., Ltd., Nishinomiya (JP)

(*) Notice: Subject to any disclaimer, the term of this patent is extended or adjusted under 35 U.S.C. 154(b) by 122 days.

(21) Appl. No.: 15/748,063

(22) PCT Filed: Jun. 8, 2016

(86) PCT No.: PCT/JP2016/066985
§ 371 (c)(1),
(2) Date: Jan. 26, 2018

(87) PCT Pub. No.: WO2017/018062
PCT Pub. Date: Feb. 2, 2017

(65) Prior Publication Data
US 2018/0209920 A1 Jul. 26, 2018

(30) Foreign Application Priority Data
Jul. 28, 2015 (JP) .................. 2015-148468

(51) Int. Cl.
*G01N 22/04* (2006.01)
*G01S 13/95* (2006.01)

(52) U.S. Cl.
CPC .............. *G01N 22/04* (2013.01); *G01S 13/95* (2013.01); *Y02A 90/18* (2018.01)

(58) Field of Classification Search
CPC ........ G01N 27/04; G01N 27/02; G01N 27/06; G01N 33/18; G01N 27/045
(Continued)

(56) References Cited

U.S. PATENT DOCUMENTS 9,910,053 B2 * 3/2018 Bakhru .............. G01N 33/4905
2014/0320144 A1 * 10/2014 Nakaya ................. H01M 10/54
324/434
(Continued)

FOREIGN PATENT DOCUMENTS

CN 102636500 A 8/2012
GB 1078111 A 8/1967
(Continued)

OTHER PUBLICATIONS

Ellis et al., "Water vapor estimates using simultaneous dual-wavelength radar observations," Radio Science, vol. 45, Oct. 2010, 15 pages.
(Continued)

*Primary Examiner* — Giovanni Astacio-Oquendo
(74) *Attorney, Agent, or Firm* — Alleman Hall Creasman & Tuttle LLP

(57) ABSTRACT

The purpose is to reliably calculate a water vapor amount at a given position. A water vapor observing apparatus may include a transmitting part (which may also be referred to as a transmitter circuitry) configured to transmit a first transmission wave and a second transmission wave having different frequencies, a receiving part (which may also be referred to as a receiver circuitry) configured to receive, as reception waves, reflection waves caused by the transmission waves reflected on and returned from a ground surface portion or a water surface after passing through water vapor, and an arithmetic processor configured to calculate an amount of the water vapor in a passing area of the transmission waves based on first reception information generated from a first reception wave obtained from the first transmission wave, and second reception information generated from a second reception wave obtained from the second transmission wave.

13 Claims, 15 Drawing Sheets

(58) Field of Classification Search
USPC .................................. 324/693, 600, 649, 691
See application file for complete search history.

(56) References Cited

U.S. PATENT DOCUMENTS

| | | | | |
|---|---|---|---|---|
| 2016/0178714 | A1* | 6/2016 | Fautz | G01R 33/483 |
| | | | | 324/309 |
| 2017/0264110 | A1* | 9/2017 | Toya | H02J 7/0021 |
| 2017/0319097 | A1* | 11/2017 | Amthor | A61B 5/055 |
| 2018/0024214 | A1* | 1/2018 | Bhat | G01R 33/4828 |
| | | | | 324/309 |

FOREIGN PATENT DOCUMENTS

| | | |
|---|---|---|
| JP | S50062083 A | 5/1975 |
| JP | H02280083 A | 11/1990 |
| JP | 2013224884 A | 10/2013 |

OTHER PUBLICATIONS

European Patent Office, Supplementary European Search Report Issued in Application No. 16830167.9, dated Feb. 18, 2019, Germany, 11 pages.
ISA Japan Patent Office, International Search Report Issued in PCT Application No. PCT/JP2016/066985, dated Aug. 23, 2016, WIPO, 4 pages. (Submitted with English Translation of International Search Report).

\* cited by examiner

WATER VAPOR OBSERVING APPARATUS

CROSS REFERENCE TO RELATED APPLICATIONS

This application is a U.S. National stage of International Application No. PCT/JP2016/066985 filed on Jun. 8, 2016, which in turn claims priority to Japanese Patent Application No. 2015-148468 filed on Jul. 28, 2015, the entire disclosure of each of which is hereby incorporated herein by reference for all purposes.

TECHNICAL FIELD

The present disclosure relates to a water vapor observing apparatus, which observes water vapor contained within atmospheric air.

BACKGROUND ART

As a conventionally-known water vapor observing apparatus, for example, Patent Document 1 discloses in claim 4 a water vapor observing apparatus including a noise measuring means for measuring, according to transmission waves discharged to a weather subject at two frequencies with different attenuation amounts or phase shift amounts caused by water vapor, levels L1 and L2 or phases $\varphi 1$ and $\varphi 2$ of reflection waves individually arriving from the weather subject to an antenna system of a weather radar, and a converting means for converting a difference between the levels (=L1−L2) or a difference between the phases ($\varphi 1 - \varphi 2$) into an amount or a distribution of water vapor in the direction of the weather subject. According to this water vapor observing apparatus, the distribution of water vapor can be obtained based on the reflection wave arrived from the weather subject. Note that, in Patent Document 1, rain cloud is exemplified as the weather subject.

REFERENCE DOCUMENTS OF CONVENTIONAL ART

Patent Document

[Patent Document 1] JP2013-224884A

DESCRIPTION OF THE DISCLOSURE

Problems to be Solved by the Disclosure

Here, since the rain cloud as the weather subject changes in position and size at every moment, when calculating the water vapor amount at a given position, it cannot be calculated if no rain cloud is located farther from the position concerned.

The present disclosure is for solving the above issue, and aims to reliably calculate a water vapor amount at a given position.

SUMMARY OF THE DISCLOSURE (1) In order to solve the above issue, a water vapor observing apparatus according to one aspect of the present disclosure may calculate an amount of water vapor contained within atmospheric air. The water vapor observing apparatus may include a transmitting part (which may also be referred to as a transmitter circuitry), a receiving part (which may also be referred to as a receiver circuitry), and an arithmetic processor. The transmitting part may transmit a first transmission wave and a second transmission wave having different frequencies. The receiving part may receive, as reception waves, reflection waves caused by the transmission waves reflected on and returned from one of a ground surface portion and a water surface after passing through the water vapor. The arithmetic processor may calculate an amount of the water vapor in a passing area of the transmission waves based on first reception information generated from a first reception wave as one of the reception waves and obtained from the first transmission wave, and second reception information generated from a second reception wave as one of the reception waves and obtained from the second transmission wave.

Note that, the ground surface portion described above may be a surface portion of the ground which includes ground surfaces, mountains, rock faces, buildings, etc. Further, the water surface may include a sea surface, a lake surface, etc.

(2) The arithmetic processor may calculate the water vapor amount in the passing area of the transmission waves based on a level difference between a first reception signal as the first reception information and a second reception signal as the second reception information.

(3) Further, the arithmetic processor may include a level difference detecting module and a water vapor amount converting module. The level difference detecting module may detect, as the level difference, a level difference between the first reception signal obtained from a reflection location on which the transmission wave reflects, and the second reception signal obtained from the reflection location. The water vapor amount converting module may convert the level difference detected by the level difference detecting module into an amount of water vapor in an area from a reference position that is an installation position of the transmitting part to the reflection location.

(4) The arithmetic processor may further include a water vapor amount calculating module configured to calculate an amount of water vapor at an arbitrary location between the reference position and the reflection location, based on the water vapor amount in the area from the reference position to the reflection location and a distance from the reference position.

(5) Further, the water vapor amount converting module may generate a cumulative water vapor amount graph by plotting the water vapor amounts in respective areas from the reference position to a plurality of the reflection locations, on coordinates that are defined by a distance position from the reference position and the water vapor amount. The water vapor amount converting module may calculate the water vapor amount at each reflection location by differentiating the cumulative water vapor amount graph.

(6) The water vapor amount converting module may calculate the water vapor amounts at two reflection locations of which azimuths with respect to the reference position are the same while distances from the transmitting part are different. The arithmetic processor may further include a water vapor amount calculating module configured to calculate a water vapor amount in an area between the two reflection locations, based on the two water vapor amounts calculated by the water vapor amount converting module.

(7) The transmitting part and the receiving part may be integrally formed to be provided as a transducer.

(8) In order to solve the above issue, a water vapor observing system according to another aspect of the present disclosure may be configured to calculate an amount of water vapor contained within atmospheric air. The water vapor observing system may include a transmitting part (which may also be referred to as a transmitter circuitry), a receiving part (which may also be referred to as a receiver circuitry), and an arithmetic processor. The transmitting part may transmit a first transmission wave and a second transmission wave having different frequencies. The receiving part may be disposed at a different position from the transmitting part and receive the transmission waves after passing through the water vapor as reception waves. The arithmetic processor may calculate an amount of the water vapor in a passing area of the transmission waves based on first reception information generated from a first reception wave as one of the reception waves and obtained from the first transmission wave, and second reception information generated from a second reception wave as one of the reception waves and obtained from the second transmission wave.

(9) The arithmetic processor may calculate the water vapor amount in the passing area of the transmission waves based on a level difference between the first reception signal as the first reception information and the second reception signal as the second reception information.

(10) Further, the water vapor observing system may include at least two of the receiving parts disposed at positions of which azimuths with respect to a reference position that is an installation position of the transmitting part are the same and distances from the transmitting part are different.

(11) The water vapor observing system may include a plurality of the receiving parts disposed in one of a lattice shape and a radial shape.

(12) The water vapor observing apparatus may further include a display unit (which may also be referred to as a display) configured to display an index of the water vapor amount calculated by the arithmetic processor.

(13) Further, the display unit may display a distribution of the water vapor amount calculated by the arithmetic processor as the index.

(14) The water vapor observing apparatus may further include an interface configured to output to an external device one of an index and a distribution of the water vapor amount calculated by the arithmetic processor.

Effect of the Disclosure

According to the present disclosure, a water vapor amount at a given position may reliably be calculated.

MODES FOR CARRYING OUT THE DISCLOSURE

Figure 1:
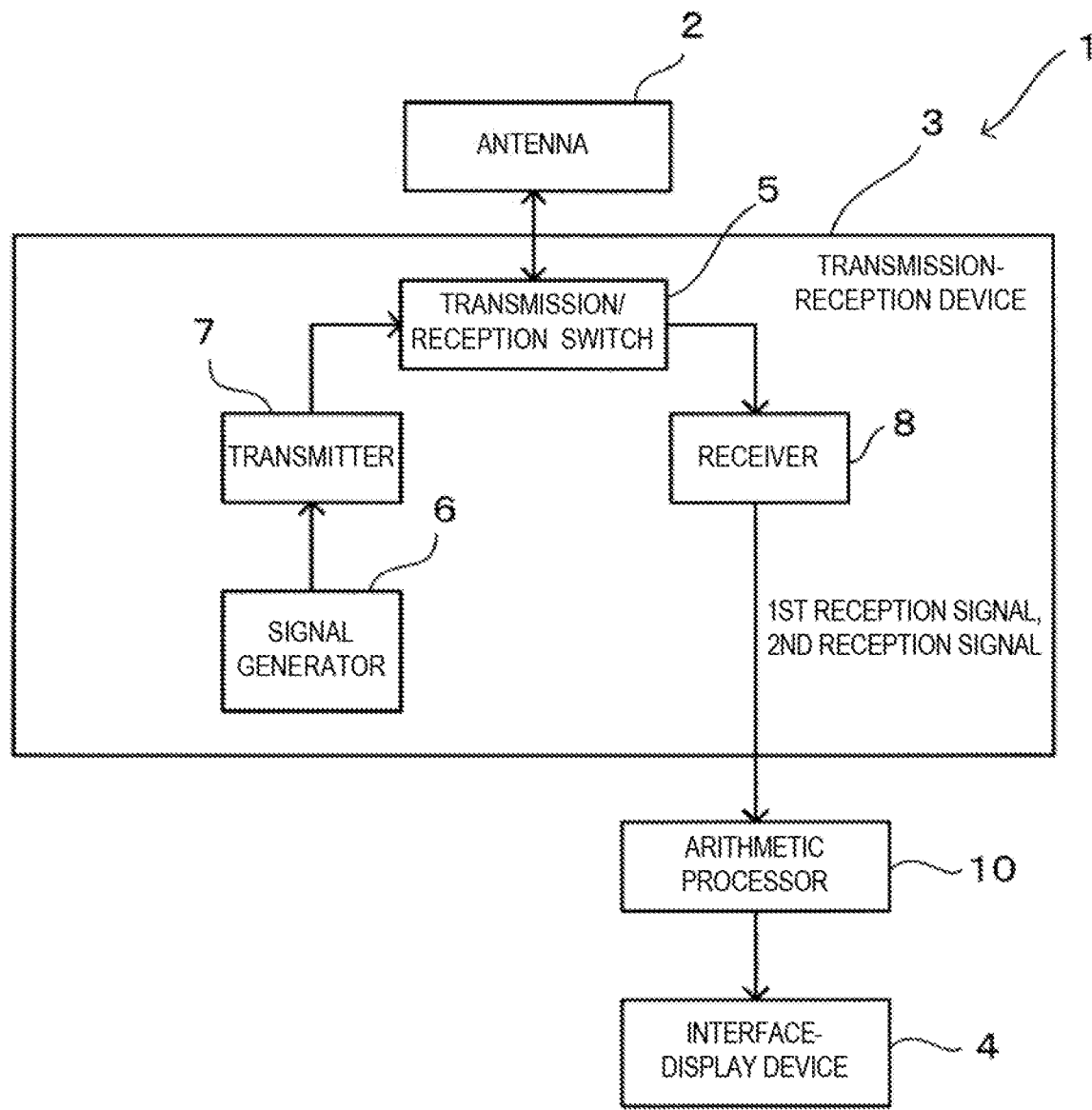
FIG. 1 is a block diagram illustrating a configuration of a water vapor observing apparatus according to one embodiment of the present disclosure.

FIG. 1 is a block diagram illustrating a configuration of a water vapor observing apparatus 1 according to one embodiment of the present disclosure. Hereinafter, the water vapor observing apparatus 1 according to the embodiment of the present disclosure is described with reference to the drawings. The water vapor observing apparatus 1 illustrated in FIG. 1 may be configured to be capable of calculating an amount of water vapor contained at respective locations within an observation area where the water vapor amount is able to be observed, to calculate a distribution of the water vapor amount within the observation area.

[Overall Configuration]

As illustrated in FIG. 1, the water vapor observing apparatus 1 may include an antenna 2, a transmission-reception device 3, an arithmetic processor 10, and an interface-display device 4 (display unit).

The antenna 2 may be a radar antenna capable of transmitting a pulse-shaped radio wave (transmission wave) with strong directivity. Further, the antenna 2 may be configured to receive a reflection wave from a target object. The transmission wave transmitted from the antenna 2, while traveling in a distance direction (a radial direction from the antenna 2), may pass through water vapor on the way, then reflect on a ground surface portion or a water surface (mainly a sea surface), and be received by the antenna 2 as the reception wave. The water vapor observing apparatus 1 may measure a time length from the transmission of the pulse-shaped radio wave until the reception of the reflection wave. Thus, the water vapor observing apparatus 1 may be capable of detecting a distance from the water vapor observing apparatus 1 (more accurately, the antenna 2) to the target object. The antenna 2 may be configured to be rotatable by 360° on a horizontal plane. The antenna 2 may be configured to repeatedly transmit and receive radio waves at every given timing while changing the transmission direction of the pulse-shaped radio wave (changing the antenna angle). With the above configuration, the water vapor observing apparatus 1 may be capable of observing the water vapor amount around the water vapor observing apparatus 1 over 360°. The reflection wave received by the antenna 2 may be outputted to a receiver 8 after being converted into a reception signal.

Note that, in the following description, operation from transmission of a pulse-shaped radio wave to transmission of a next pulse-shaped radio wave may be referred to as "sweep." Further, the operation of rotating the antenna 360° while transmitting and receiving the radio wave may be referred to as "scanning."

Further, the antenna 2 may be configured to be capable of transmitting and receiving two kinds of transmission waves and two kinds of reception waves having different frequencies from each other. In this embodiment, the antenna 2 may transmit a first transmission wave having a frequency of about 10 GHz and a second transmission wave having a frequency of about 22 GHz. The first transmission wave and the second transmission wave transmitted from the antenna 2 may reflect on the ground surface portion or the water surface after passing through water vapor and be received by the antenna 2 as a first reception wave and a second reception wave, respectively. The first and second transmission waves may be transmitted alternately or simultaneously. Further, the first reception wave and the second reception wave received by the antenna 2 may be converted into a first reception signal (first reception information) and a second reception signal (second reception information), respectively.

Here, the reason for using the transmission wave having the frequency of about 10 GHz and the second transmission wave having the frequency of about 22 GHz as described above in this embodiment is described. In an attenuation constant of an electromagnetic wave having the frequency of about 10 GHz (lower than 0.01 dB/km), a portion attributable to water vapor may be extremely small. Thus, the 10 GHz transmission wave may not greatly attenuate due to water vapor even by traveling through the water vapor. On the other hand, in an attenuation constant of an electromagnetic wave having the frequency of about 22 GHz (about 0.3 dB/km), a portion attributable to water vapor may be relatively large. Thus, the second transmission wave may greatly attenuate due to water vapor as it travels through the water vapor. In the water vapor observing apparatus 1 according to this embodiment, although is described later in detail, the water vapor amount at each location may be estimated using this characteristic.

The transmission-reception device 3 may include a transmission/reception switch 5, a signal generator 6, a transmitter 7, and the receiver 8. When transmitting, the transmission/reception switch 5 may switch its connection so that a transmission signal is transmitted from the transmitter 7 to the antenna 2. Further, when receiving, the transmission/reception switch 5 may switch its connection so that the reception signal (electric signal) from the antenna 2 is transmitted to the receiver 8.

The signal generator 6 may generate transmission signals to be the basis of the first transmission wave and the second transmission wave for the antenna 2 to transmit. The transmission signals may be amplified by the transmitter 7 and then outputted to the antenna 2 via the transmission/reception switch 5.

The receiver 8 may amplify the reception signals (the first reception signal and the second reception signal) outputted from the antenna 2 and A/D convert the amplified reception signals. Then, the receiver 8 may output the reception signals converted into digital signals, to the arithmetic processor 10.

Figure 2:
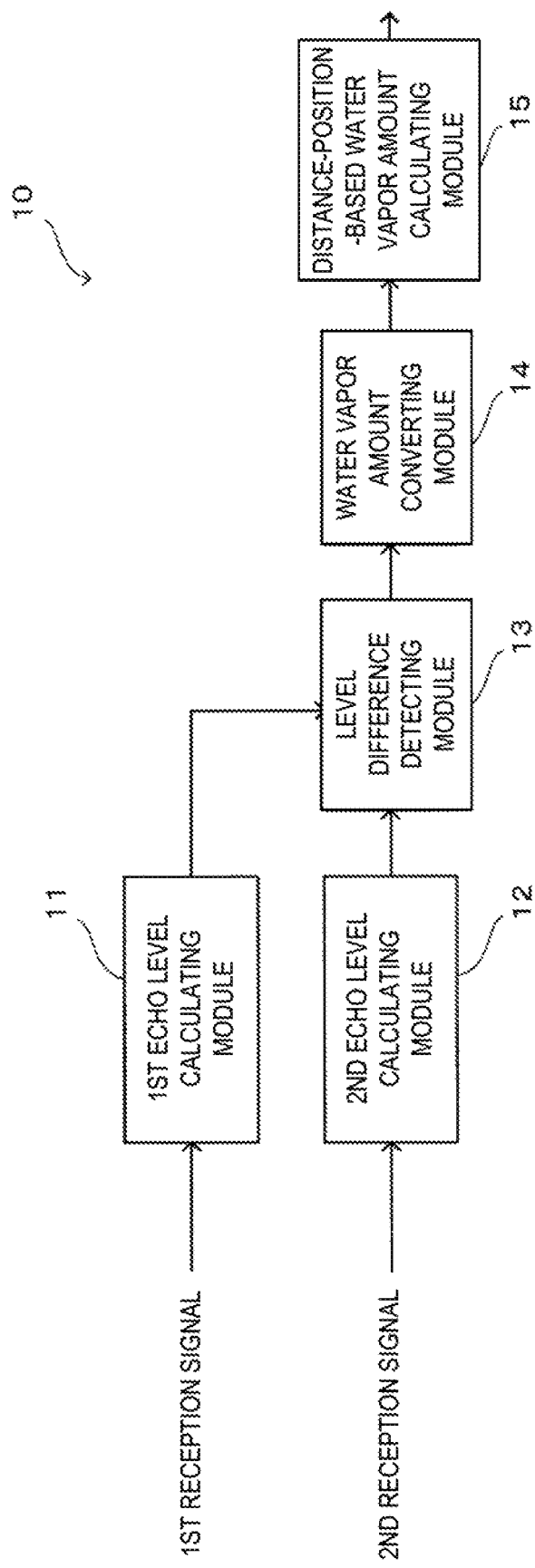
FIG. 2 is a block diagram illustrating a configuration of an arithmetic processor illustrated in FIG. 1.

FIG. 2 is a block diagram illustrating a configuration of the arithmetic processor 10 illustrated in FIG. 1. The arithmetic processor 10 may be configured to calculate the water vapor amount at each location in the observation area based on the first reception signal and the second reception signal outputted from the receiver 8. As illustrated in FIG. 2, the arithmetic processor 10 may include a first echo level calculating module 11, a second echo level calculating module 12, a level difference detecting module 13, a water vapor amount converting module 14, and a distance-position-based water vapor amount calculating module 15. The arithmetic processor 10 may be comprised of devices such as a non-illustrated processor (CPU, FPGA, etc.) and a memory, for example. For example, the CPU may read a program from the memory and execute it to cause the arithmetic processor 10 to function as the first echo level calculating module 11, the second echo level calculating module 12, the level difference detecting module 13, the water vapor amount converting module 14, and the distance-position-based water vapor amount calculating module 15.

Figure 3A:
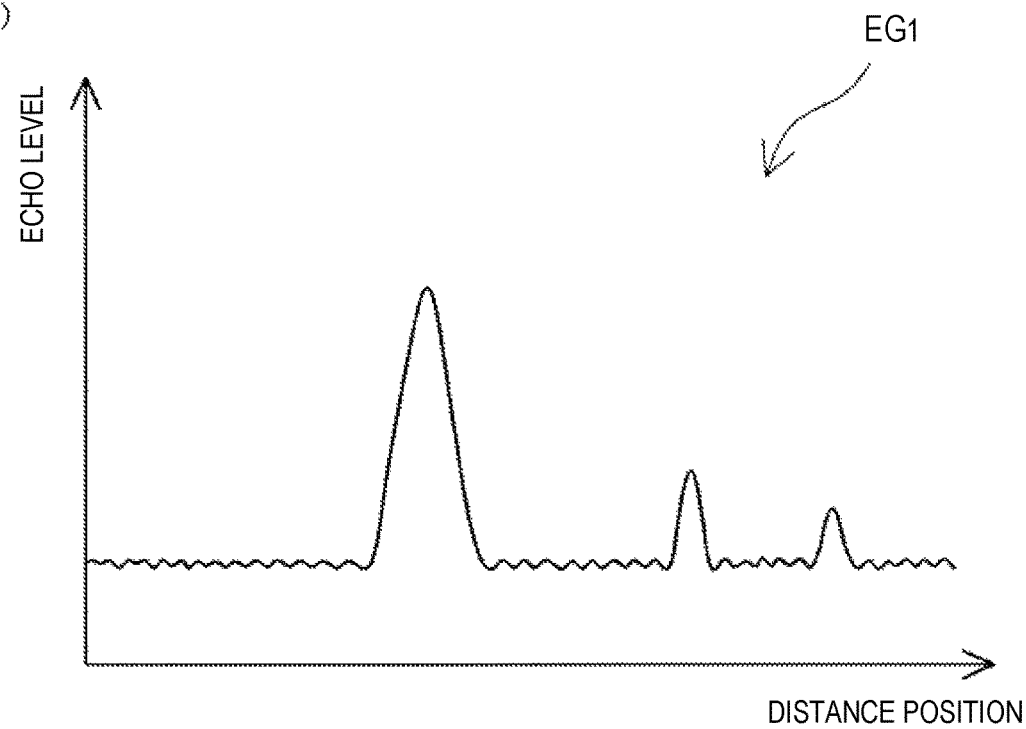
FIG. 3(A) is a chart illustrating a first echo graph generated based on a first reception signal.

Based on the reception signal (first reception signal) obtained from the reflection wave of the first transmission wave (first reception wave) arriving from each azimuth with respect to a reference position being an installation position of the antenna 2, the first echo level calculating module 11 may calculate a level of an echo (signal intensity) from each distance position at the azimuth. FIG. 3(A) is a graph in which each sample constituting an echo signal from a certain azimuth is plotted on coordinates of which a horizontal axis is a distance position and a vertical axis is an echo level of the echo signal returned from each distance position (first echo graph $EG_1$). The first echo level calculating module 11 may generate the first echo graph $EG_1$ as illustrated in FIG. 3(A) for each azimuth. Note that, when the antenna is used as a reference, the distance position described above may refer to a position away from the antenna 2 by a distance concerned. For example, a position where the distance position at a certain azimuth is 1 km may be a position along the certain azimuth and 1 km away from the antenna 2.

Figure 3B:
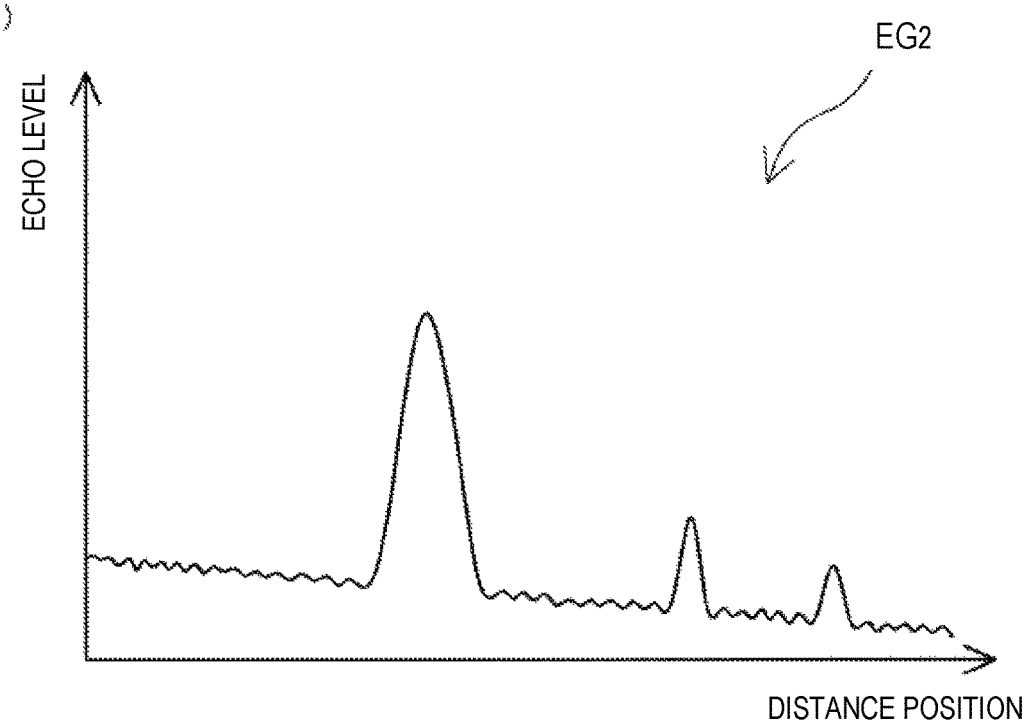
FIG. 3(B) is a chart illustrating a second echo graph generated based on a second reception signal.

The second echo level calculating module 12 may calculate an echo level from each distance position at each azimuth based on the reception signal (second reception signal) obtained from the reflection wave of the second transmission wave (second reception wave) arriving from each azimuth with respect to the antenna 2. FIG. 3(B) is a graph in which each sample constituting an echo signal from a certain azimuth is plotted on coordinates of which a horizontal axis is the distance position and a vertical axis is an echo level of the echo signal returned from each distance position (second echo graph $EG_2$). The second echo level calculating module 12 may generate the second echo graph $EG_2$ as illustrated in FIG. 3(B) for each azimuth.

Figure 4A:
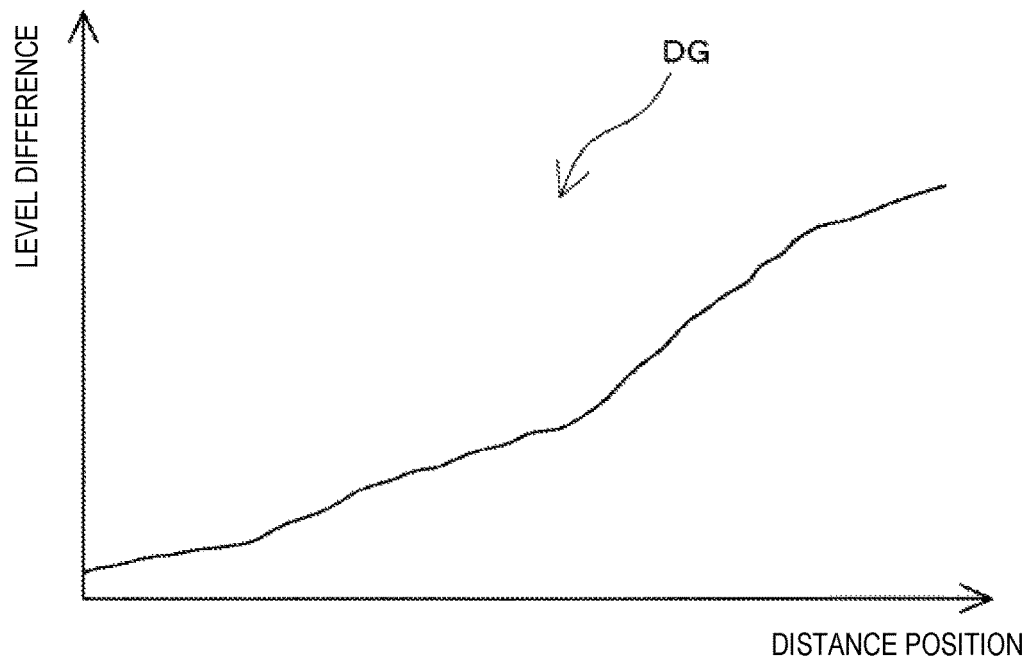
FIG. 4(A) is a chart illustrating a level difference graph.

The level difference detecting module 13 may detect a level difference $\Delta Lv$ between the echo level, calculated by the first echo level calculating module 11, of the first reception wave returned from a certain location (reflection location), and the echo level, calculated by the second echo level calculating module 12, of the second reception wave returned from the certain location. The level difference detecting module 13 may calculate the level difference $\Delta Lv$ at each location in the observation area. FIG. 4(A) is a graph in which the level difference ΔLv calculated for each distance position at a certain azimuth is plotted on coordinates of which a horizontal axis is the distance position and a vertical axis is the level difference ΔLv at each distance position (level difference graph DG). That is, the graph illustrated in FIG. 4(A) may be a graph generated by taking a difference between the first echo graph $EG_1$ illustrated in FIG. 3(A) and the second echo graph $EG_2$ illustrated in FIG. 3(B). The level difference detecting module 13 may generate the level difference graph DG as illustrated in FIG. 4 for each azimuth.

Figure 4B:
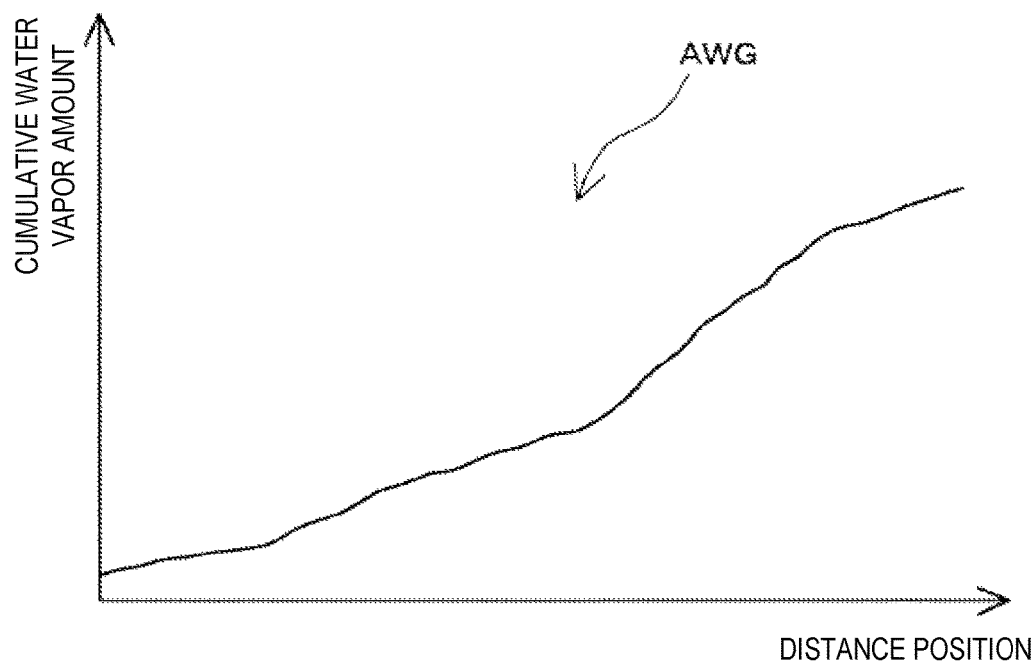
FIG. 4(B) is a chart illustrating a cumulative water vapor amount graph.

FIG. 4(B) is a graph generated by the water vapor amount converting module 14, corresponding to FIG. 4(A) with the vertical axis converted into the water vapor amount. The water vapor amount converting module 14 may convert the level difference ΔLv at each location which is detected by the level difference detecting module 13 into the water vapor amount. Specifically, the water vapor amount converting module 14 may utilize that the level difference ΔLv at each distance position and the water vapor amount within a range from the reference position (the position of the antenna 2) to each distance position are in a correspondence relationship, to convert the level difference ΔLv at each distance position into the water vapor amount within the range to each distance position. In the graph generated by the water vapor amount converting module 14 (see FIG. 4(B)), a horizontal axis indicates the distance position and a vertical axis indicates the water vapor amount within the range from the reference position to the respective distance position. That is, this graph may be generated as a cumulative water vapor amount graph AWG in which the water vapor amount gradually increases in the horizontal-axis direction.

Figure 5:
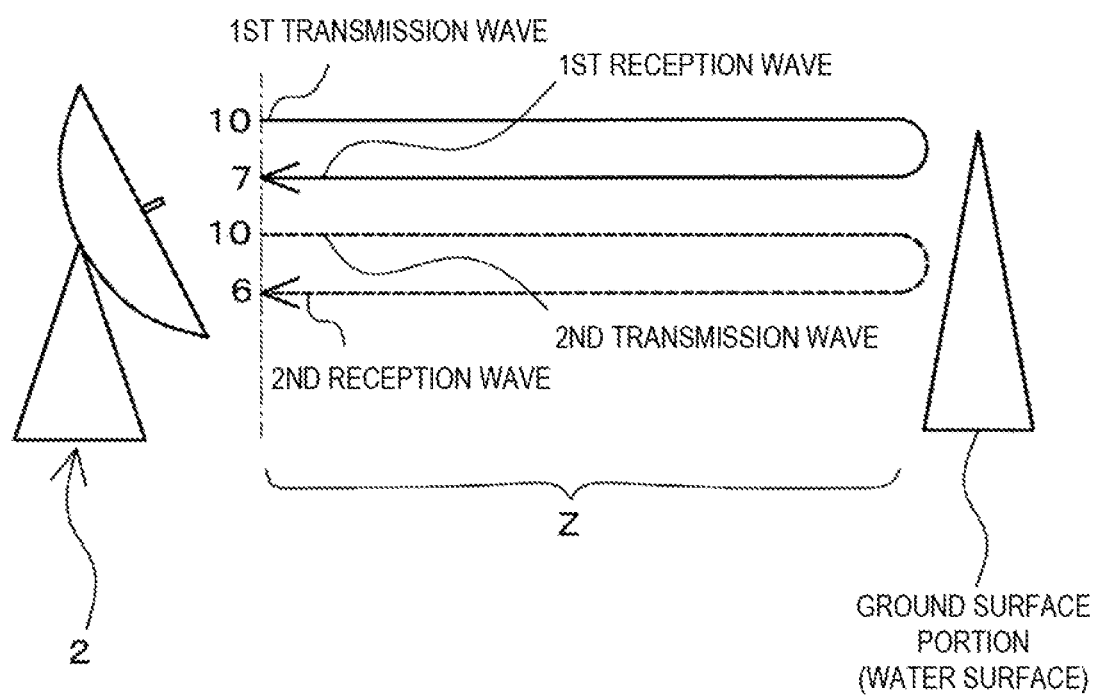
FIG. 5 is a view schematically illustrating first and second transmission waves transmitted from an antenna, and first and second reception waves reflected on and returned from a particular reflection target (a ground surface portion or a water surface).

Here, the reason of the level difference at each distance position and the water vapor amount within the range from the antenna 2 to each distance position being in the correspondence relationship is described. FIG. 5 is a view schematically illustrating the first and second transmission waves transmitted from the antenna 2 and the first and second reception waves reflected on and returned from a particular reflection target (a ground surface portion or a water surface). FIG. 5 shows an example in which the echo intensities of the first and second transmission waves are 10, the echo intensity of the first reception wave is 7, and the echo intensity of the second reception wave is 6. Note that, although FIG. 5 schematically illustrates the ground surface portion (or the water surface) in a triangular shape, actually, the ground surface portion (or the water surface) extends in the traveling directions of the transmission and reception waves.

As described above, the electromagnetic wave having the frequency of about 10 GHz may not attenuate greatly due to water vapor. Therefore, a difference between the echo intensity 10 of the first transmission wave and the echo intensity 7 of the first reception wave (that is, the attenuation amount of the first transmission wave) may be considered to be attributable to a factor other than water vapor. On the other hand, the electromagnetic wave having the frequency of about 22 GHz may greatly attenuate due to water vapor. Therefore, a difference between the echo intensity 10 of the second transmission wave and the echo intensity 6 of the second reception wave (that is, the attenuation amount of the second transmission wave) may be considered to be attributable to water vapor and a factor other than water vapor. Thus, the level difference ΔLv between the echo intensity 7 of the first reception wave and the echo intensity 6 of the second reception wave may be considered to be attributable to the water vapor amount within a passing area Z of the transmission wave. As a result, the level difference ΔLv and the water vapor amount within the range from the antenna 2 to each distance position may be considered to have a correspondence relationship.

Figure 6:
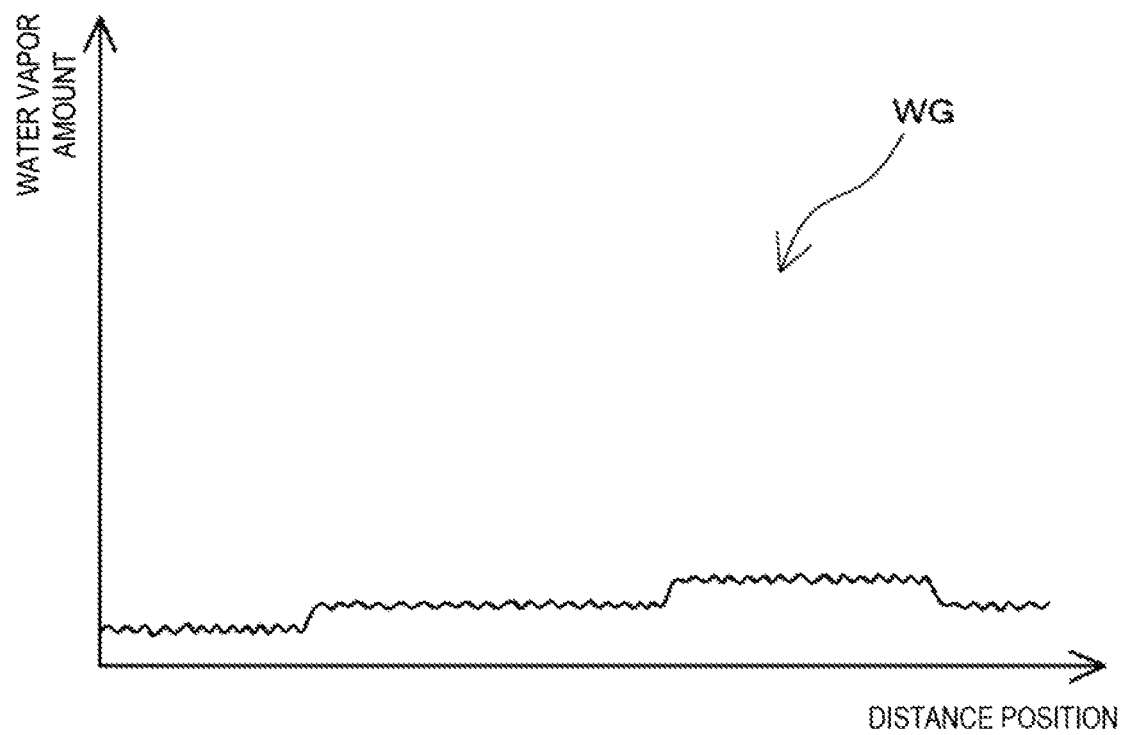
FIG. 6 is a chart illustrating a distance-position-based water vapor amount graph.

FIG. 6 is a graph illustrating a distance-position-based water vapor amount graph WG generated by the distance-position-based water vapor amount calculating module 15, which is obtained by differentiating the graph illustrated in FIG. 4(B) (cumulative water vapor amount graph AWG) for each distance position. The distance-position-based water vapor amount calculating module 15 may generate the distance-position-based water vapor amount graph WG by differentiating the cumulative water vapor amount graph AWG which is generated by the water vapor amount converting module 14 in the distance direction. The distance-position-based water vapor amount calculating module 15 may generate the distance-position-based water vapor amount graphs WG for respective azimuths with respect to the antenna 2, and integrate them to generate a water vapor distribution map DM indicating the water vapor amounts at distance positions at respective azimuths with respect to the antenna 2.

Figure 7:
FIG. 7 is a view illustrating one example of a water vapor distribution map displayed on an interface-display device, illustrating a part thereof in an enlarged manner.

FIG. 7 is a view illustrating one example of the water vapor distribution map DM displayed on the interface-display device 4, illustrating a part thereof in an enlarged manner. As illustrated in FIG. 7, the interface-display device 4 may display the water vapor distribution map DM generated by the distance-position-based water vapor amount calculating module 15. The interface-display device 4 may display in a color tone corresponding to the water vapor amount, each location on a map including the location where the water vapor observing apparatus 1 is installed. Thus, a user can grasp the water vapor amount at each location on the map. Note that in FIG. 7, the above-described color tone may be illustrated in association with the density of dots. Specifically, high density dots may be displayed at locations where the water vapor amount is large, and low density dots may be displayed at locations where the water vapor amount is small.

[Effect]

As described above, in the water vapor observing apparatus 1 according to this embodiment, the water vapor amount in the passing area of the electromagnetic wave may be calculated based on the first reception signal and the second reception signal obtained from the reflection waves of the electromagnetic waves in two frequency bands (around 10 GHz and 22 GHz) having different degrees of attenuation due to water vapor. In this manner, the attenuation amount of the transmission wave due to the factor other than water vapor may be removed and extraction of only the attenuation amount of the transmission wave due to water vapor may become possible. Thus, the water vapor amount in the passing area of the electromagnetic wave may be calculated.

Additionally, according to the water vapor observing apparatus 1, the reflection wave reflected on and returned from the ground surface portion or the water surface after passing through water vapor may be received as the reception wave. A surface portion of the Earth may be considered to be comprised of the ground surface portion and the water surface (mainly the sea surface). Thus, upon suitable selection of the installation position of the antenna 2, calculation of the water vapor amount over the entire area on the ground may become possible by calculating the water vapor amount based on the reflection waves from the ground surface portion and the water surface.

Therefore, according to the water vapor observing apparatus 1, the water vapor amount at a desired position may reliably be calculated.

Further according to the water vapor observing apparatus 1, the water vapor amount in the passing area of the electromagnetic wave may be calculated based on the level difference between the first and second reception signals. In this manner, the attenuation amount of the transmission wave due to the factor other than water vapor may suitably be removed, thus only the attenuation amount of the transmission wave due to water vapor may be extracted. Thus, the water vapor amount in the passing area of the electromagnetic wave may be calculated.

Further according to the water vapor observing apparatus 1, the water vapor amount in the area from the installation position of the antenna 2 to the reflected location of the reception signal may suitably be calculated by using the level difference detecting module 13 and the water vapor amount converting module 14.

Further according to the water vapor observing apparatus 1, since the antenna 2 as a transducer configured to be capable of transmitting and receiving an electromagnetic wave may be provided, the part which transmits the electromagnetic wave and the part which receives the electromagnetic wave may be integrated. As a result, the water vapor observing apparatus 1 may entirely be reduced in size.

Further according to the water vapor observing apparatus 1, the level difference ΔLv at each location at the same azimuth with respect to the position of the antenna 2 may be detected and converted into the water vapor amount. Due to the above-described correspondence relationship between the level difference ΔLv and the water vapor amount within the range from the antenna 2 to each distance position, the water vapor amount within the range from the antenna 2 to each distance position may suitably be calculated by detecting the level difference ΔLv.

Further according to the water vapor observing apparatus 1, the water vapor amount at each location may be calculated by differentiating the cumulative water vapor amount graph AWG. Thus, the water vapor amount at each location may suitably and easily be calculated.

Further according to the water vapor observing apparatus 1, the water vapor amount at each location may be indicated by the color tone as an index expressing the water vapor amount. Thus, the user can easily grasp the water vapor amount at each location.

Further according to the water vapor observing apparatus 1, the water vapor distribution map DM indicating the water vapor amounts at distance positions at respective azimuths with respect to the antenna 2 may be displayed on the interface-display device 4. Thus, the user can grasp the distribution of water vapor within the observation area.

[Modification]

Although the embodiment of the present disclosure is described above, the present disclosure is not limited thereto, and various modifications are possible without departing from the scope of the present disclosure.

Figure 8:
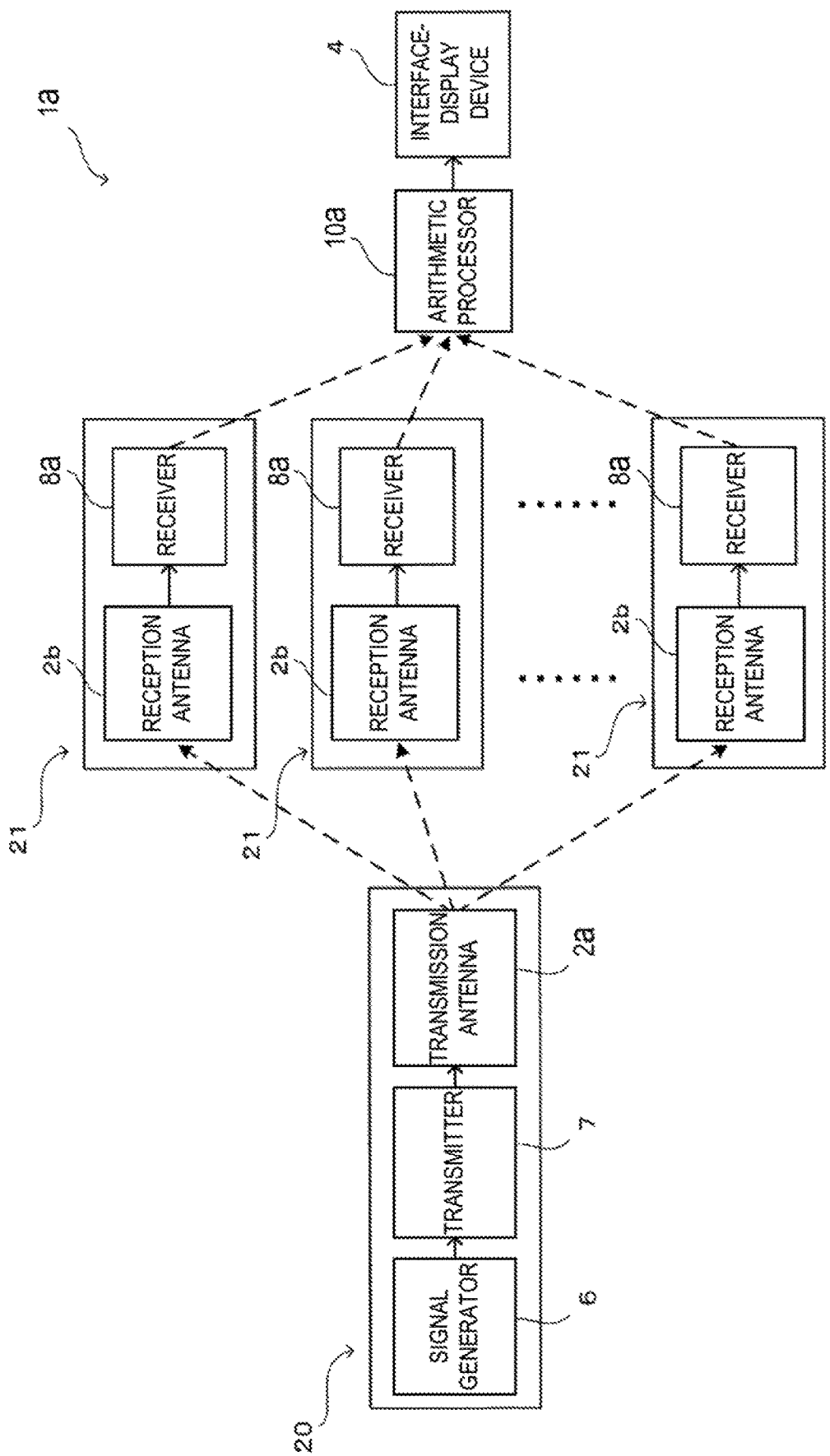
FIG. 8 is a block diagram illustrating a configuration of a water vapor observing apparatus according to a modification.
Figure 9:
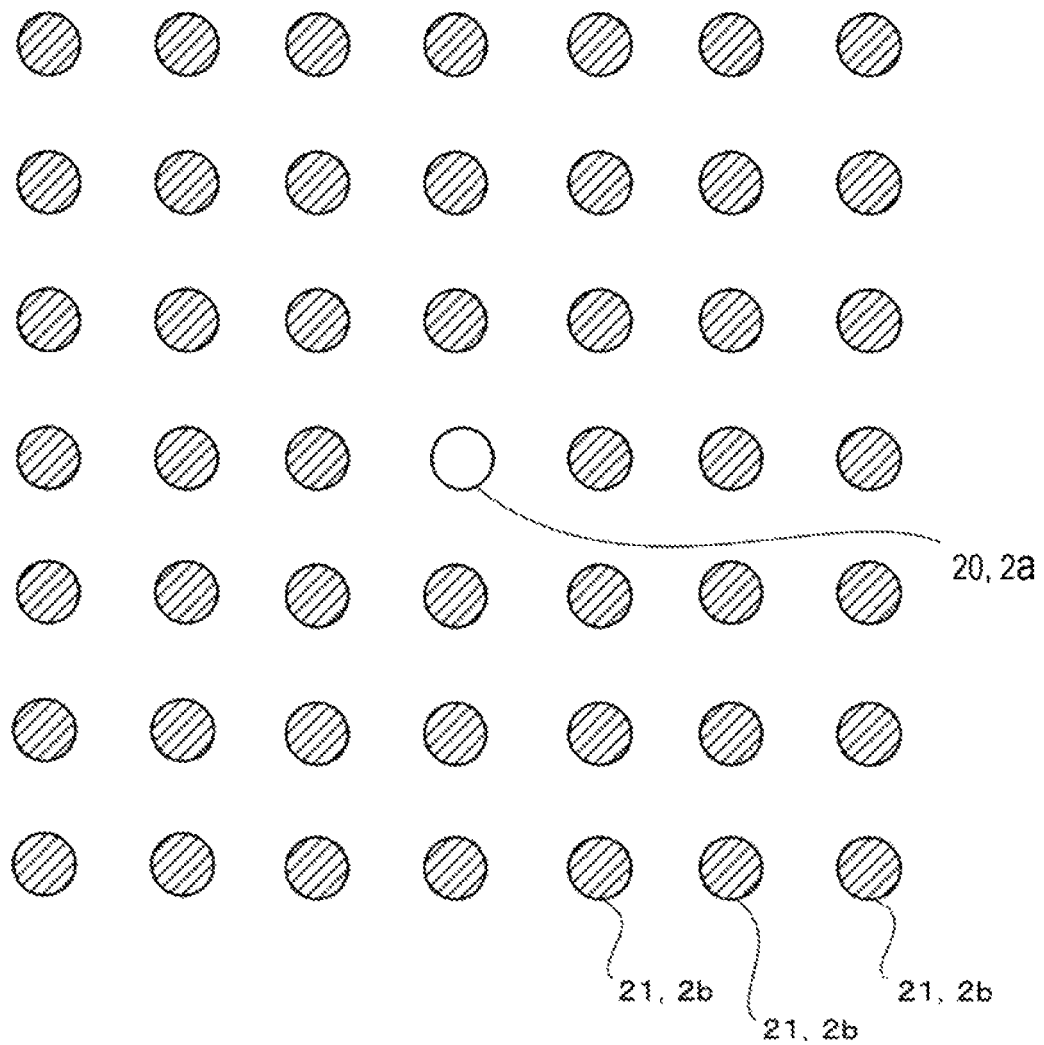
FIG. 9 is a plan view schematically illustrating a positional relationship of a transmission unit with reception units illustrated in FIG. 8.

(1) FIG. 8 is a block diagram illustrating a configuration of a water vapor observing apparatus 1a (which may also be referred to as a water vapor observing system 1a) according to a modification. Further, FIG. 9 is a plan view schematically illustrating a positional relationship of a transmission unit 20 (transmission antenna 2a) with reception units 21 (reception antennas 2b) illustrated in FIG. 8. FIG. 9 schematically illustrates the position of the transmission unit 20 with a circle without hatching, and the positions of the reception units 21 with hatched circles. The water vapor observing apparatus 1a of this modification may include the transmission unit 20 which is a unit on the side for transmitting the transmission wave, the plurality of reception units 21 which are units on the side for receiving the reception wave, an arithmetic processor 10a, an interface-display device 4.

The transmission unit 20 may include the transmission antenna 2a, a signal generator 6, and a transmitter 7. The transmission antenna 2a may be to transmit the transmission wave and, similarly to the antenna 2 of the above embodiment, configured to be capable of transmitting the first transmission wave and the second transmission wave. In the transmission unit 20, transmission signals generated by the signal generator 6 to be the basis of the first and second transmission waves may be amplified by the transmitter 7 and then outputted to the antenna 2a.

Each of the reception units 21 may be disposed at a position different from that of the transmission unit 20. As illustrated in FIG. 9, the reception units 21 may be arranged in a lattice shape with the transmission unit 20 as the center. Each reception unit 21 may include the reception antenna 2b and a receiver 8a.

The reception antenna 2b may be to receive the reception wave and, similarly to the antenna 2 of the above embodiment, configured to be capable of receiving the first reception wave and the second reception wave. The reception wave received by the reception antenna 2b, similarly to the case of the above embodiment, may be converted into the first reception signal and the second reception signal, then amplified and A/D converted by the corresponding receiver 8a, and transmitted to the arithmetic processor 10a wirelessly, for example.

Figure 10:
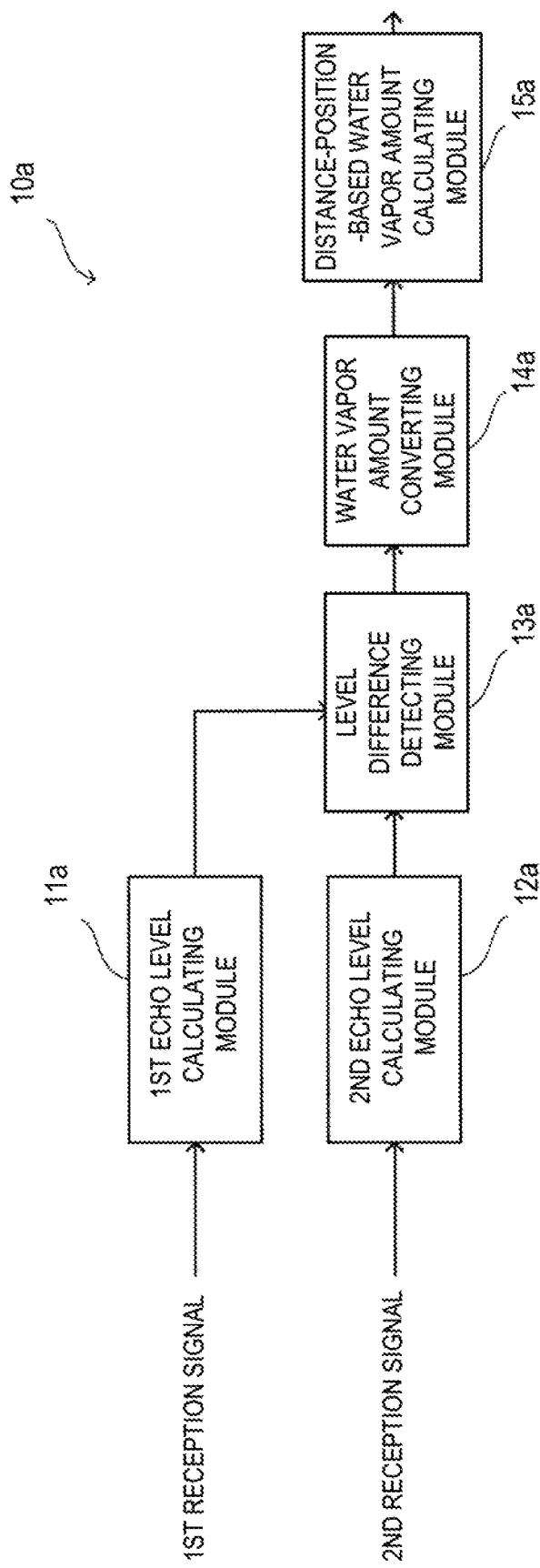
FIG. 10 is a block diagram illustrating a configuration of an arithmetic processor illustrated in FIG. 8.
Figure 11:
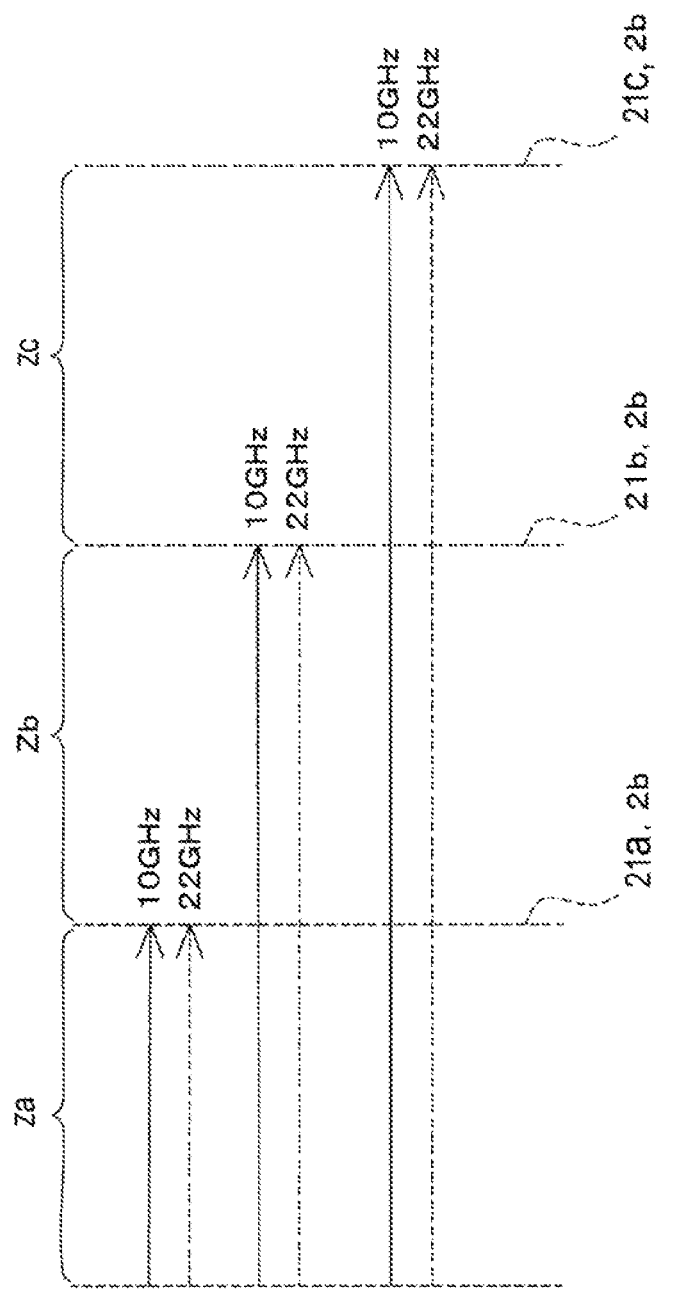
FIG. 11 is a view schematically illustrating a situation where first and second transmission waves transmitted by a transmission antenna are received as reception waves by respective reception antennas.
Figure 11:
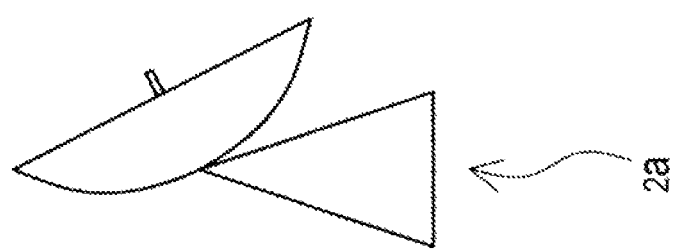

FIG. 10 is a block diagram illustrating a configuration of the arithmetic processor illustrated in FIG. 8. Further, FIG. 11 is a view schematically illustrating a situation where the first and second transmission waves transmitted by the transmission antenna 2a are received as reception waves by the respective reception antennas 2b. Note that, FIG. 11 schematically illustrates, with dashed lines, the positions of the reception units arranged substantially in line at the same azimuth. Further in FIG. 11, the reference characters of the reception units are made 21a, 21b and 21c in this order from the transmission antenna 2a side.

As illustrated in FIG. 10, the arithmetic processor 10a may include a first echo level calculating module 11a, a second echo level calculating module 12a, a level difference detecting module 13a, a water vapor amount converting module 14a, and a distance-position-based water vapor amount calculating module 15a.

The first echo level calculating module 11a may calculate the echo level of the first reception signal obtained from the first reception wave resulted from the first transmission wave, which is transmitted from the transmission antenna 2a, arriving at the reception antenna 2b. The first echo level calculating module 11a may calculate the echo level of the first reception signal obtained by each of the reception antennas 2b.

The second echo level calculating module 12a may calculate the echo level of the second reception signal obtained from the second reception wave resulted from the second transmission wave which is transmitted from the transmission antenna 2a, arriving at the reception antenna 2b. The second echo level calculating module 12a may calculate the echo level of the second reception signal obtained by each of the reception antennas 2b.

The level difference detecting module 13a may detect the level difference between the echo level of the first reception signal obtained by each reception antenna 2b and the echo level of the second reception signal obtained by the same reception antenna 2b.

The water vapor amount converting module 14a may convert the level difference for every reception unit 21, detected by the level difference detecting module 13, into the water vapor amount. Specifically, the water vapor amount converting module 14 may utilize that the level difference detected for each reception unit 21 and the water vapor amount within the range from the transmission unit 20 to each reception unit 21 are in the correspondence relationship, to convert the level difference detected for each reception unit 21 into the water vapor amount within the range from the transmission unit 20 to each reception unit 21.

The distance-position-based water vapor amount calculating module 15a may calculate a difference between water vapor amounts calculated by the adjacent units among the reception units 21 arranged substantially in line at the same azimuth (in the example illustrated in FIG. 11, the reception units 21a and 21b, the reception units 21b and 21c) to calculate the water vapor amount at each location in the observation area (each small sub-area included in the observation area). Specifically, with reference to FIG. 11, the distance-position-based water vapor amount calculating module 15a may calculate a difference between the water vapor amount calculated by the reception unit 21b (that is, the water vapor amount in the areas Za and Zb) and the water vapor amount calculated by the reception unit 21a (that is, the water vapor amount in the area Za) to calculate the water vapor amount in the area Zb. Similarly, the distance-position-based water vapor amount calculating module 15a may calculate a difference between the water vapor amount calculated by the reception unit 21c (that is, the water vapor amount in the areas Za, Zb and Zc) and the water vapor amount calculated by the reception unit 21b (that is, the water vapor amount in the areas Za and Zb) to calculate the water vapor amount in the area Zc. The distance-position-based water vapor amount calculating module 15a may also perform similar processing for the other reception units adjacent to each other in the azimuth. Thus, the water vapor observing apparatus 1a of this modification may also calculate the water vapor amount at each location in the observation area similarly to the case of the water vapor observing apparatus 1 of the above embodiment.

[Effect]

As described above, in the water vapor observing apparatus 1a of this modification, the transmission antenna 2a and the reception antennas 2b may be disposed at different positions. Further, the water vapor amount in the passing area of the reception wave may be calculated based on the difference between the first and second reception waves with different frequencies which are received by the reception antennas 2b. In the case of the water vapor observing apparatus 1a, the arrangement of the reception antennas 2b may be set to sandwich with the transmission antenna 2a the area where the water vapor amount is to be calculated, so as to reliably calculate the water vapor amount at a desired position.

Further in the water vapor observing apparatus 1a, two reception antennas 2b (e.g., see FIG. 11, the reception antennas of the reception units 21a and 21b and the reception antennas of the reception units 21b and 21c) may be disposed so that the azimuth with respect to the transmission antenna 2a becomes the same and the distance from the transmission antenna 2a becomes different. In the case of the water vapor observing apparatus 1a, by arranging these two reception antennas 2b to sandwich the area where the water vapor amount is to be calculated, the water vapor amount at a desired position may reliably be calculated regardless of the position of the transmission antenna 2a.

Further in the water vapor observing apparatus 1a, since the reception antennas 2b may be arranged in the lattice shape, the water vapor amount in each small sub-area of the area where the reception antennas 2b are arranged in the lattice shape may be calculated.

Figure 12:
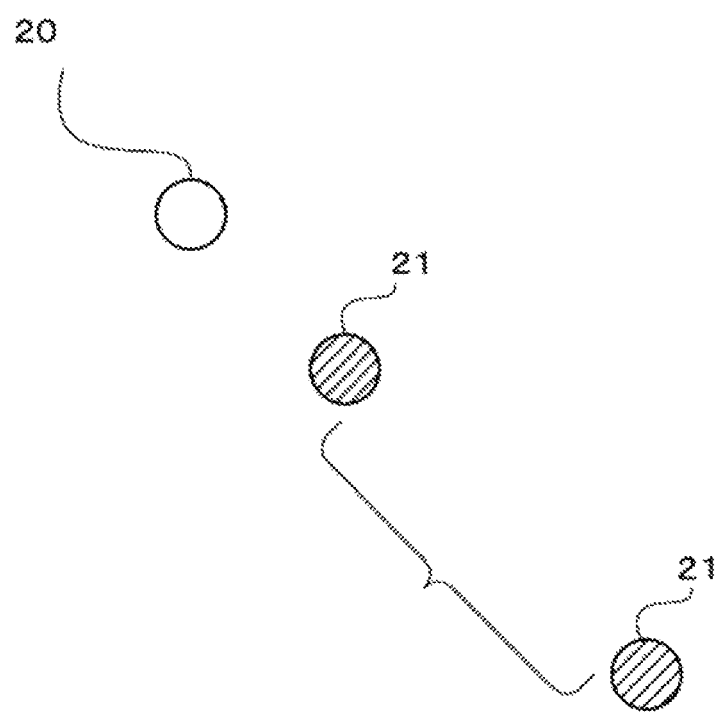
FIG. 12 is a plan view schematically illustrating a positional relationship of transmission unit with reception units provided to a water vapor observing apparatus according to a modification, in correspondence to FIG. 9.

(2) FIG. 12 is a plan view schematically illustrating a positional relationship of a transmission unit 20 with reception units 21 of a water vapor observing apparatus according to a modification, in correspondence to FIG. 9. Although the reception units 21 may be arranged in a lattice shape in the modification illustrated in FIGS. 8 and 9, it is not limited to this. Specifically, as illustrated in FIG. 12, two reception units 21 may be arranged at positions at the same azimuth with respect to the transmission unit 20 but at different distances therefrom. In this modification, for example, by arranging the two reception units 21 to sandwich the area where the water vapor amount is to be observed, the water vapor amount in a desired area may be observed while reducing the number of required reception units 21.

(3) Although in the above embodiment the transmission of the transmission wave and the reception of the reception wave may be performed by a single antenna 2, without limiting to this, a transmission antenna and a reception antenna may be provided and disposed at different positions.

(4) Although in the above embodiment the electromagnetic wave having the frequency of about 10 GHz and the electromagnetic wave having the frequency of about 22 GHz may be used as the transmission waves, it is not limited to this. Specifically, electromagnetic waves of any frequency bands may be used as transmission waves as long as parts of attenuation constants thereof caused by water vapor are different.

Figure 13:
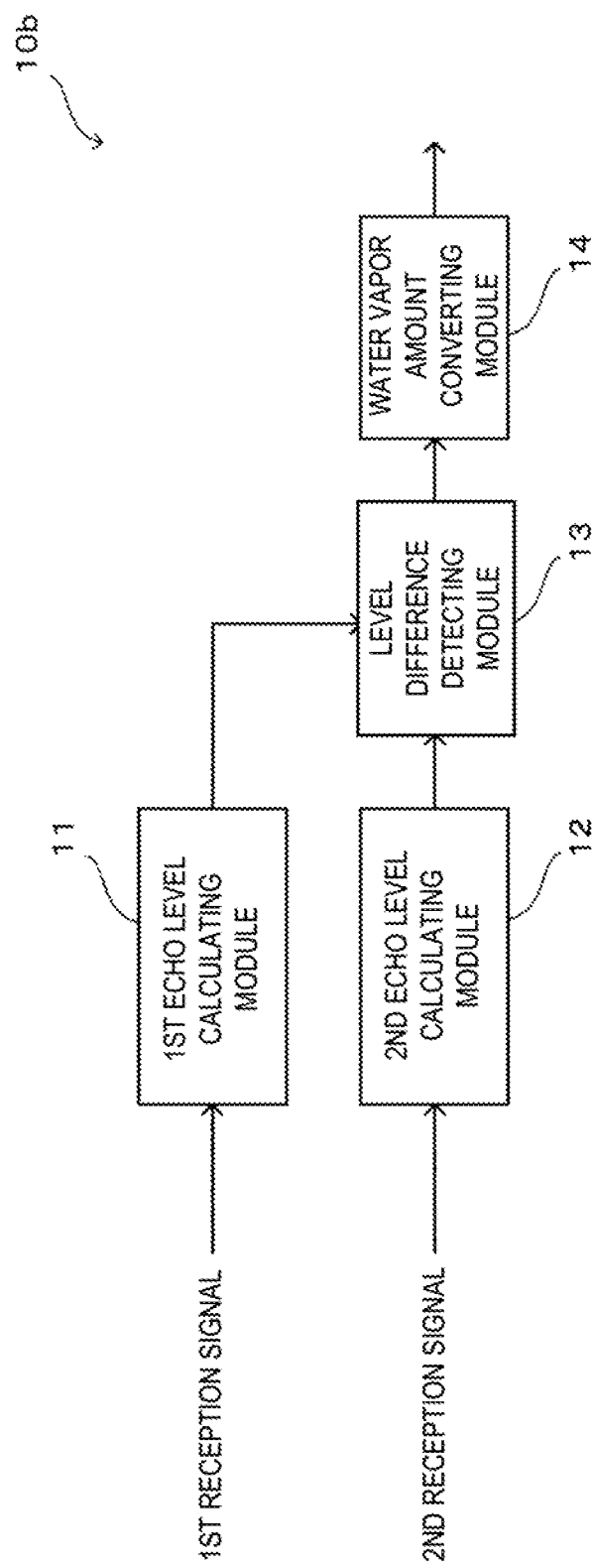
FIG. 13 is a block diagram illustrating a configuration of an arithmetic processor of the water vapor observing apparatus according to a modification.

(5) FIG. 13 is a block diagram illustrating a configuration of an arithmetic processor 10b of a water vapor observing apparatus according to a modification. Although in the above embodiment the distance-position-based water vapor amount calculating module 15 may be provided to calculate the water vapor amount at each location in the observation area, it is not limited to this. Specifically, as in this modification, a configuration in which the distance-position-based water vapor amount calculating module 15 is omitted may be adopted. In this case, the water vapor amount in the area from the position of the antenna 2 to each location may be calculated at each azimuth.

(6) Although in the water vapor observing apparatus 1 of the above embodiment, the cumulative water vapor amount graph AWG (see FIG. 4(B)) may be differentiated in the distance direction to calculate the water vapor amount at each distance position for each azimuth, without limiting to this, the level difference $\Delta Lv$ may be detected at two locations so that the difference between these level differences $\Delta Lv$ may be taken in the calculation of the water vapor amount. Here, by selecting the above-described two locations so as to sandwich the area where the water vapor amount is to be calculated, the water vapor amount in the desired area may be calculated without providing a plurality of reception antennas as illustrated in FIG. 8.

(7) Although in the above embodiment the example in which the water vapor distribution map DM may be displayed on the interface-display device 4 is given, it is not limited to this. Specifically, for example, the interface-display device 4 may display the water vapor amount at a particular location as a numerical value.

Figure 14:
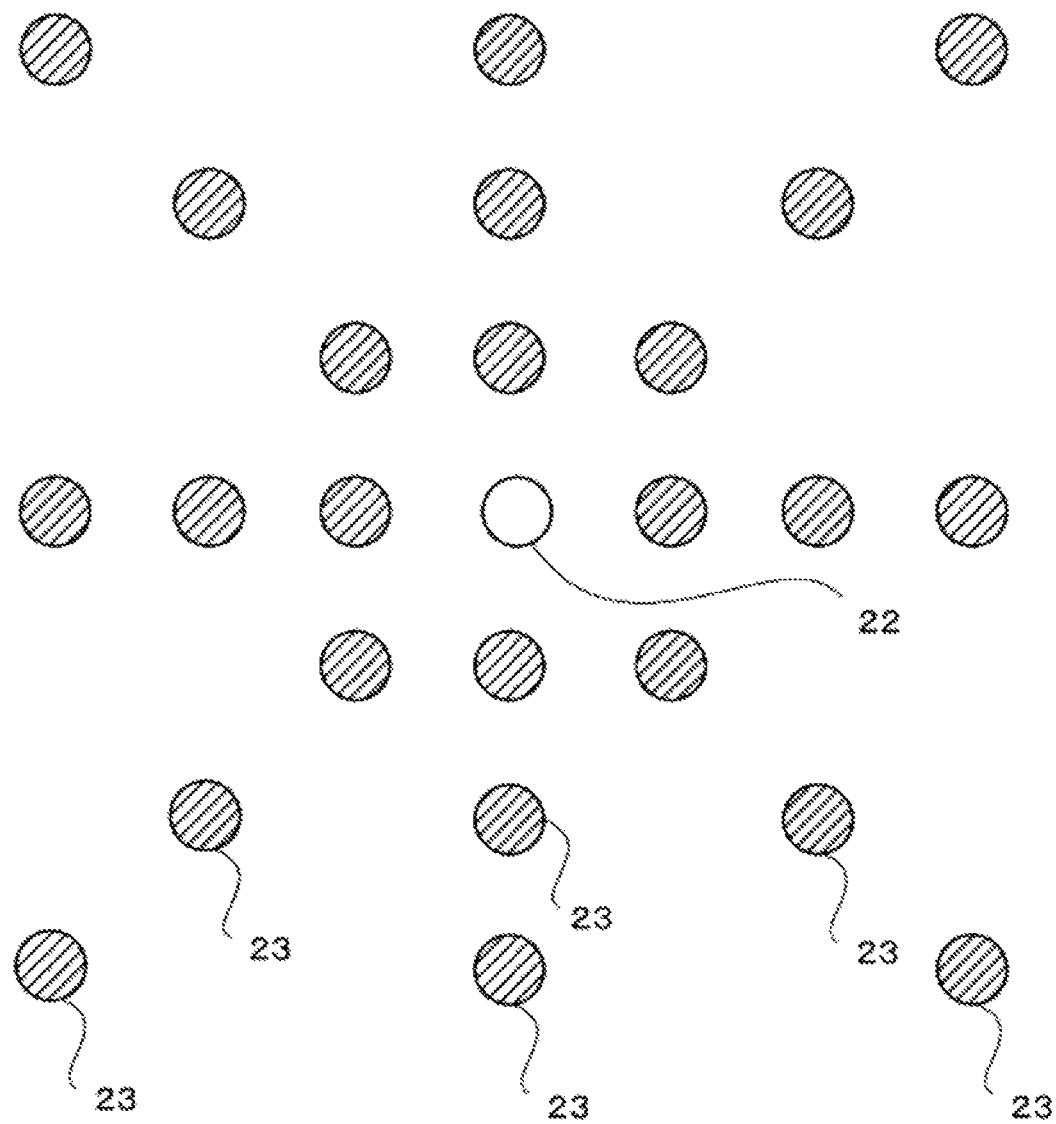
FIG. 14 is a view schematically illustrating a positional relationship of a transmission unit with reception units provided to a water vapor observing apparatus according to a modification, in correspondence to FIG. 9.

(8) FIG. 14 is a view schematically illustrating a positional relationship of a transmission unit 22 with reception units 23 of a water vapor observing apparatus according to a modification, in correspondence to FIG. 9. Although the reception units 21 may be arranged in the lattice shape (as illustrated in FIG. 9) in the modifications illustrated in FIGS. 8 and 11, other arrangements may be applied without limiting to this. Specifically, as illustrated in FIG. 14, the reception units 23 may be arranged radially centering on the transmission unit 22. Further, the reception units may be arranged three dimensionally instead of two dimensionally.

Figure 15:
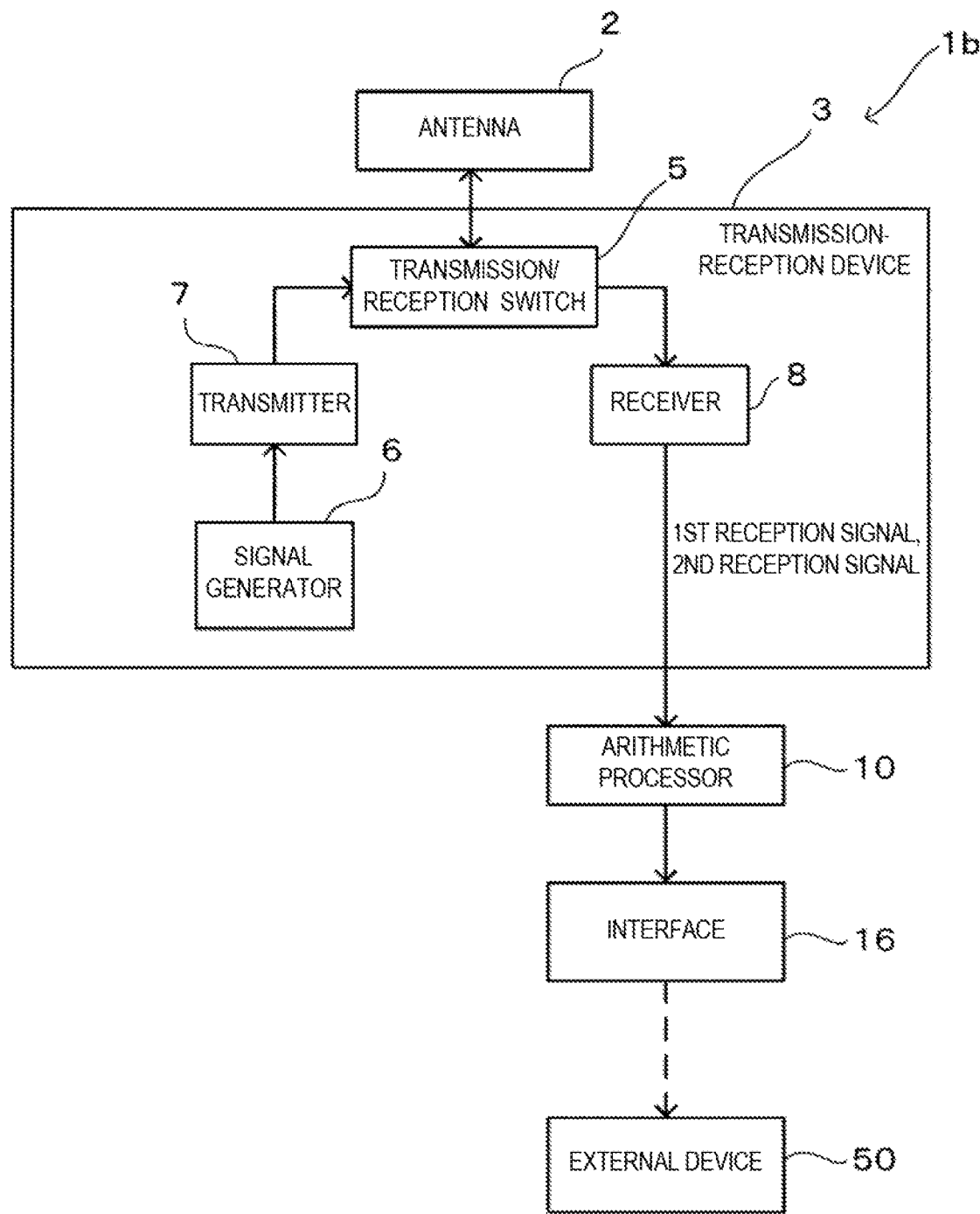
FIG. 15 is a block diagram illustrating a configuration of a water vapor observing apparatus according to a modification.

(9) FIG. 15 is a block diagram illustrating a configuration of a water vapor observing apparatus 1b according to a modification. Compared with the water vapor observing apparatus 1 of the above embodiment, the water vapor observing apparatus 1b of this modification may not be provided with the interface-display device 4, but alternatively be provided with an interface 16 configured to output data regarding the water vapor distribution map DM to an external device 50. One example of the interface 16 may be a connector to which a cable is connected. One example of the external device 50 may be a display configured to display the water vapor distribution map DM. According to the water vapor observing apparatus 1b, information on the water vapor amount calculated by the arithmetic processor 10 may be displayed on the external device.

DESCRIPTION OF REFERENCE CHARACTERS 1, 1a, 1b Water Vapor Observing Apparatus
2 Antenna (Transmitting Part, Receiving Part, Transducer)
2a Transmission Antenna (Transmitting Part)
2b Reception Antenna (Receiving Part)
10, 10a, 10b Arithmetic Processor

The invention claimed is:

1. A water vapor observing apparatus for calculating an amount of water vapor contained within atmospheric air, comprising:
a transmitter circuitry configured to transmit a first transmission wave and a second transmission wave having different frequencies;
a receiver circuitry configured to receive, as reception waves, reflection waves caused by the transmission waves reflected on and returned from one of a ground surface portion and a water surface after passing through the water vapor; and
an arithmetic processor configured to calculate an amount of the water vapor in a passing area of the transmission waves based on first reception information generated from a first reception wave obtained from the first transmission wave, and a second reception information generated from a second reception wave obtained from the second transmission wave.

2. The water vapor observing apparatus of claim 1, wherein the arithmetic processor calculates the water vapor amount in the passing area of the transmission waves based on a level difference between a first reception signal as the first reception information and a second reception signal as the second reception information.

3. The water vapor observing apparatus of claim 2, wherein the arithmetic processor is configured to:
detect a level difference between the first reception signal obtained from a reflection location on which the transmission wave reflects, and the second reception signal obtained from the reflection location; and
convert the level difference detected into an amount of water vapor in an area from a reference position that is an installation position of the transmitter circuitry to the reflection location.

4. The water vapor observing apparatus of claim 3, wherein the arithmetic processor is further configured to calculate an amount of water vapor at an arbitrary location between the reference position and the reflection location, based on the water vapor amount in the area extending from the reference position to the reflection location and a distance of the arbitrary location from the reference position.

5. The water vapor observing apparatus of claim 4, wherein, the arithmetic processor is further configured to;
generate a cumulative water vapor amount graph by plotting the water vapor amounts in respective areas from the reference position to a plurality of the reflection locations, on coordinates that are defined by a distance position from the reference position and the water vapor amount, and
calculate the water vapor amount at each reflection location by differentiating the cumulative water vapor amount graph.

6. The water vapor observing apparatus of claim 3, wherein, the arithmetic processor is processor is further configured to;
calculate the water vapor amounts at two reflection locations of which azimuths with respect to the reference position are the same while distances from the transmitter circuitry are different, and
calculate a water vapor amount in an area between the two reflection locations, based on the two water vapor amounts calculated.

7. The water vapor observing apparatus of claim 1, wherein the transmitter circuitry and the receiver circuitry are integrally formed to be provided as a transducer.

8. The water vapor observing apparatus of claim 1, further comprising a display configured to display an index of the water vapor amount calculated by the arithmetic processor.

9. The water vapor observing apparatus of claim 8, wherein the display displays a distribution of the water vapor amount calculated by the arithmetic processor as the index.

10. The water vapor observing apparatus of claim 1, further comprising an interface configured to output to an external device one of an index and a distribution of the water vapor amount calculated by the arithmetic processor.

11. A water vapor observing system for calculating an amount of water vapor contained within atmospheric air, comprising:
a transmitter circuitry configured to transmit a first transmission wave and a second transmission wave having different frequencies;
a receiver circuitry positioned at a different position from the transmitter circuitry and configured to receive the transmission waves after passing through the water vapor as reception waves; and
an arithmetic processor configured to calculate an amount of the water vapor in a passing area of the transmission waves based on a first reception information generated from a first reception wave obtained from the first transmission wave, and a second reception information generated from a second reception wave obtained from the second transmission wave, wherein
the arithmetic processor calculates the water vapor amount in the passing area of the transmission waves based on a level difference between a first reception signal as the first reception information and a second reception signal as the second reception information.

12. The water vapor observing system of claim 11, comprising at least two of the receiver circuitry positioned at positions of which azimuths with respect to a reference position that is an installation position of the transmitter circuitry are the same and distances from the transmitter circuitry are different.

13. The water vapor observing system of claim 11, comprising a plurality of the receiver circuitries positioned in one of a lattice shape and a radial shape.

* * * * *